(12) United States Patent
Usala et al.

(10) Patent No.: US 6,315,994 B2
(45) Date of Patent: Nov. 13, 2001

(54) MEDIUM AND MATRIX FOR LONG-TERM PROLIFERATION OF CELLS

(76) Inventors: Anton-Lewis Usala, 237 Buckingham Dr., Winterville, NC (US) 28590; Richard Chris Klann, 239 E. Main St., Washington, NC (US) 27889

(*) Notice: Subject to any disclaimer, the term of this patent is extended or adjusted under 35 U.S.C. 154(b) by 24 days.

(21) Appl. No.: 09/758,793

(22) Filed: Jan. 11, 2001

Related U.S. Application Data

(60) Division of application No. 09/113,437, filed on Jul. 10, 1998, now Pat. No. 6,231,881, which is a continuation-in-part of application No. 08/568,482, filed on Dec. 7, 1995, now Pat. No. 5,834,005, which is a continuation-in-part of application No. 08/300,429, filed on Sep. 2, 1994, now abandoned, which is a continuation-in-part of application No. 07/841,973, filed on Feb. 24, 1992, now abandoned.

(51) Int. Cl.$^7$ ................................................ A61K 35/39

(52) U.S. Cl. .................... 424/93.7; 424/424; 424/492; 514/772; 514/774; 435/182; 623/11.11

(58) Field of Search .................... 424/93.7, 424, 424/492; 514/772, 774; 435/182; 623/11.11

(56) References Cited

U.S. PATENT DOCUMENTS

| | | |
|---|---|---|
| 4,198,479 | 4/1980 | Tytell et al. . |
| 4,477,567 | 10/1984 | Healy et al. . |
| 4,520,821 | 6/1985 | Schmidt et al. . |
| 4,657,866 | 4/1987 | Kumar . |
| 4,696,286 | 9/1987 | Cochrum . |
| 4,797,213 | 1/1989 | Parisius et al. . |
| 4,863,856 | 9/1989 | Dean, Jr. et al. . |
| 4,868,121 | 9/1989 | Scharp et al. . |
| 4,902,295 | 2/1990 | Walthall et al. . |
| 4,950,483 | 8/1990 | Ksander et al. . |
| 4,978,616 | 12/1990 | Dean, Jr. et al. . |
| 4,997,753 | 3/1991 | Dean, Jr. et al. . |
| 5,021,349 | 6/1991 | Drouet et al. . |
| 5,079,160 | 1/1992 | Lacy et al. . |
| 5,100,783 | 3/1992 | Dean, Jr. et al. . |
| 5,116,753 | 5/1992 | Beattie et al. . |
| 5,132,223 | 7/1992 | Levine et al. . |
| 5,322,790 | 6/1994 | Scharp et al. . |
| 5,405,772 | 4/1995 | Ponting . |
| 5,605,938 | 2/1997 | Roufa et al. . |
| 5,645,591 | 7/1997 | Kuberasampath et al. . |
| 5,672,361 | 9/1997 | Halberstadt et al. . |
| 5,681,587 | 10/1997 | Halberstadt et al. . |
| 5,716,404 | 2/1998 | Vacanti et al. . |
| 5,824,331 | 10/1998 | Usala . |
| 5,830,492 | 11/1998 | Usala . |
| 5,834,005 | 11/1998 | Usala . |
| 5,840,059 | 11/1998 | March et al. . |

FOREIGN PATENT DOCUMENTS

| | | |
|---|---|---|
| 44 31 598 A1 | 3/1996 | (DE) . |
| 0 213 908 A2 | 3/1987 | (EP) . |
| 0 481 791 A2 | 4/1992 | (EP) . |
| 0 526 756 A | 2/1993 | (EP) . |
| 0 564 786 A | 10/1993 | (EP) . |
| 0 363 125 A2 | 10/1998 | (EP) . |
| WO91/09119 A1 | 6/1991 | (WO) . |
| WO92/19195 | 11/1992 | (WO) . |
| WO93/00441 | 1/1993 | (WO) . |
| WO93/16685 | 9/1993 | (WO) . |
| WO93/24112 A1 | 12/1993 | (WO) . |
| WO94/03154 A1 | 2/1994 | (WO) . |
| WO94 08702 | 4/1994 | (WO) . |
| WO94/15589 A1 | 7/1994 | (WO) . |
| WO95/14037 | 5/1995 | (WO) . |
| WO95/19430 A1 | 7/1995 | (WO) . |
| WO95/29231 | 11/1995 | (WO) . |
| WO97 02569 A | 6/1997 | (WO) . |
| WO97 39107 | 10/1997 | (WO) . |
| WO98/04681 | 2/1998 | (WO) . |
| WO98/16629 | 4/1998 | (WO) . |

OTHER PUBLICATIONS

Donofrio, "The Effects of Growth Factors on Proliferation of Adult Porcine Islets In Vitro", Department of Biology, East Carolina University (May 1997).

Hubbell, et al., "Tissue Engineering," Chemical & Engineering News, (Mar. 13, 1995), pp. 42–54.

Metrakos et al., "Collagen Gel Matrix Promotes Islet Cell Proliferation," Transplantation Proceedings, vol. 26, No. 6 (Dec. 1994) pp. 3349–3350.

Mandel et al., "Organ Culture of Fetal Mouse and Fetal Human Pancreatic Islets for Allografting," Diabetes, vol. Suppl. 4(Aug. 1982), pp. 39–47.

Isner, et al., "Therapeutic Angiogenesis," Frontiers in Bioscience, vol. 3 (May 5, 1998) pp. 49–69.

*Primary Examiner*—Francisco Prats
*Assistant Examiner*—Brett Ozga
(74) *Attorney, Agent, or Firm*—Alston & Bird LLP

(57) ABSTRACT

A cell culture medium and hydrogel matrix for long term storage and proliferation of cells is provided. The cell culture medium and hydrogel matrix include an effective amount of polar amino acids, the polar amino acids selected from the group consisting of arginine, lysine, histidine, glutamic acid, and aspartic acid. The cell culture medium comprises about 5 to about 150 mM of polar amino acids. The hydrogel matrix comprises about 3 to about 150 mM of polar amino acids. Arginine and glutamic acid are preferably supplemented in the cell culture medium. Arginine, lysine, and glutamic acid are preferably supplemented in the hydrogel matrix. A method of maintaining viability and functioning of a transplant is also provided. The method of maintaining viability of a transplant includes encapsulating the cells in a hydrogel matrix and injecting the encapsulated cells into the host organism. The matrix of the present invention may also be used to promote vascularization in a transplant site prior to injection of cells.

36 Claims, 4 Drawing Sheets

Porcine C-Peptide after Injection of Porcine Tissue in Matrix

| Week | 0 | 1 | 2 | 3 | 4 | 5 | 6 | 7 | 8 | 9 | 10 | 11 | 12 | 13 |
|---|---|---|---|---|---|---|---|---|---|---|---|---|---|---|
| Rabbit 3 | <0.1 | 0.2 | 0.2 | | 0.1 0.2(t=0-40) 0.3(t=50,60) | <0.1 | 0.1 | <0.1 | 0.1(t=0,1) | <0.1 | 0.1 | 0.1 | <0.1 | necropsy |
| Dog 22136 | <0.1 | <0.1 | 0.2 | <0.1, 0.1(t=60) | 0.1(15pts) | 0.1(7pts) 0.2(t=15) | 0.1(t=0-80) 0.2(t=90) | pancreatectomy | | | | | | |

| Week | 0 | 1 | 2 | 3 | 4 | 5 | 6 | 7 | 8 | 9 | 10 | 11 | 12 | 13 |
|---|---|---|---|---|---|---|---|---|---|---|---|---|---|---|
| Rabbit 6 | <0.1 | <0.1 0.1 | 0.1 | <0.1 | <0.1 | 0.1 | <0.1 | <0.1 | <0.1 | 0.1 | 0.2 | <0.1(t=0) | 0.2 | <0.1 |
| | 14 | 15 | 16 | 17 | 18* | 19 | 20 | 21 | 22 | 23 | 24 | 25 | 26 | 27 |
| | 0.1 | <0.1 | 0.1 | <0.1 | 0.1 | <0.1 | <0.1 | 0.1 | 0.1, <0.1 | <0.1 | <0.1 | <0.1 | 0.1 | necropsy |
| | | | | | | | 0.1 (t=0,1,5,80,90) | | | | | | | |

FIG. 1

IN VITRO INSULIN PULSATILITY
AS A FUNCTION OF ISLET PURITY

95% ISLET PURITY

Device SN 970122-1
Islet Number: 231,300

85% ISLET PURITY

Device SN 970129-1
Islet Number: 256,770

50% ISLET PURITY

Device SN 970116-1
Islet Number: 235,500

Insulin Collection in Perifusion:

(as a function of islet number, purity and age)

FIG. 3

| Device Number | Performance in Perifusion | | Device Characteristics | | | |
|---|---|---|---|---|---|---|
| | Under 2 hrs. | | Islet Age (Days) | # Islets (kEIN) | Islet/Matrix Volume (ml) | Islet Purity (%) |
| | Insulin Collected (Units) | μU/Islet Collected | | | | |
| 970404-1 | 3.65 | 397 | 6 | 9.2 | 0.2 | 38 |
| -2 | 3.5 | 380 | 6 | 9.2 | 0.2 | 38 |
| -3 | 8.42 | 458 | 6 | 18.4 | 0.4 | 38 |
| -9 | 8.48 | 461 | 6 | 18.4 | 0.4 | 38 |
| -5 | 0.99 | 135 | 5 | 7.4 | 0.2 | 31 |
| -6 | 0.81 | 110 | 5 | 7.4 | 0.2 | 31 |
| -7 | 2.64 | 180 | 5 | 14.7 | 0.4 | 31 |
| -8 | 3.58 | 244 | 5 | 14.7 | 0.4 | 31 |

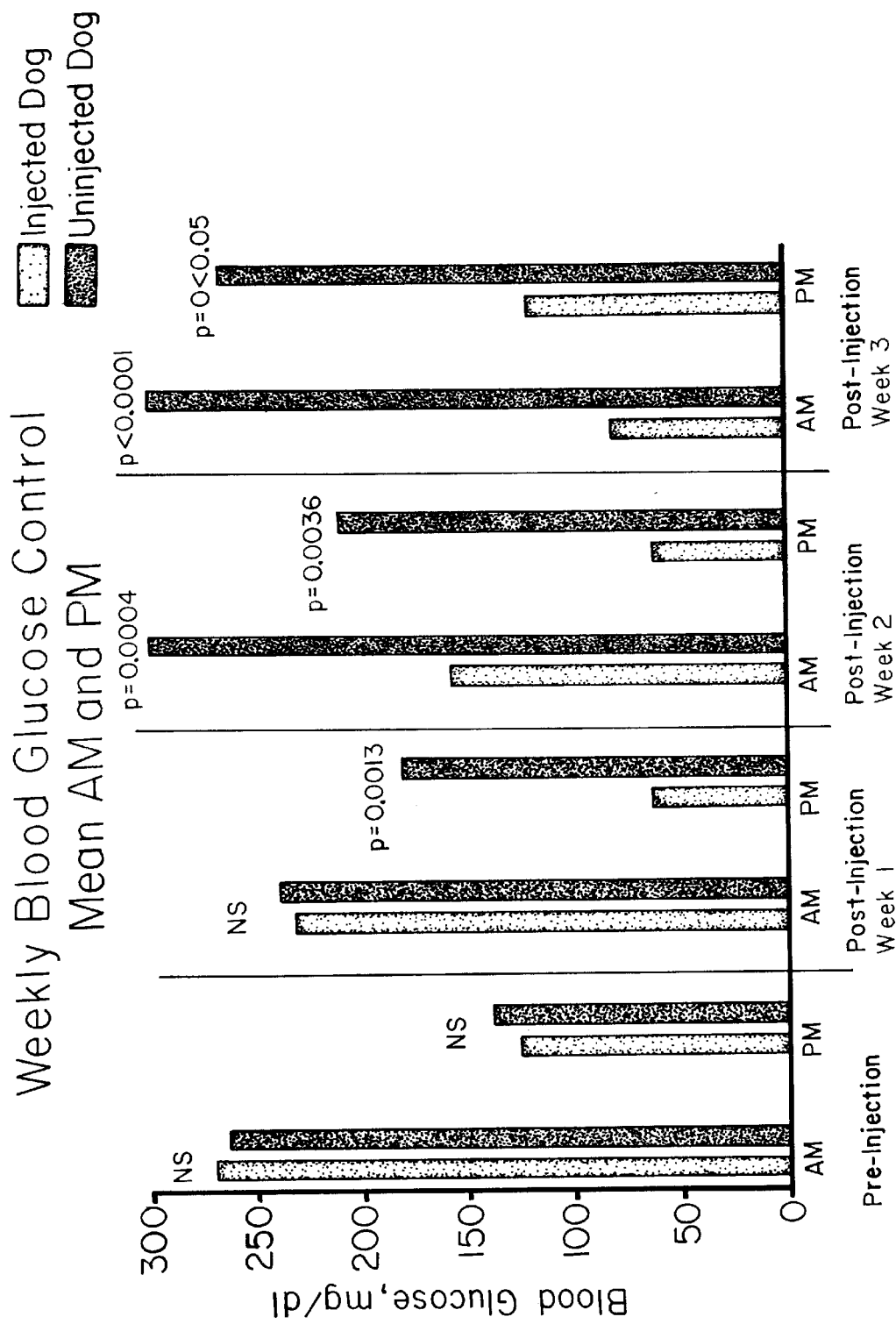

MEDIUM AND MATRIX FOR LONG-TERM PROLIFERATION OF CELLS

CROSS-REFERENCE TO RELATED APPLICATIONS

This application is a divisional of U.S. application Ser. No. 09/113,437, filed Jul. 10, 1998, now U.S. Pat. No. 6,231,881 which is incorporated by reference in its entirety, which is a continuation-in-part of application Ser. No 08/568,482, filed Dec. 7, 1995, now U.S. Pat. No. 5,834,005, which is a continuation-in-part of application Ser. No. 08/300,429, filed Sep. 2, 1994, now abandoned, which is a continuation-in-part of application Ser. No. 07/841,973, filed Feb. 24, 1992, now abandoned.

FIELD OF INVENTION

The present invention relates to a cell culture medium and matrix composition for preserving cell viability as well as gene expression and specialized tissue function. The present invention also relates to a matrix capable of sustaining cell viability after injection of hormone secreting cellular moieties into living tissue.

BACKGROUND OF THE INVENTION

New methods for treating insulin-dependant diabetes mellitus are presently being sought. At the present time, diabetes patients test their blood sugar levels and inject insulin when necessary. Although it is possible to transplant a pancreas from one human to another, the survival rate for this procedure is only 40% at one year following surgery. Researchers have used isolated pancreatic islets in transplantation approaches in attempts to find a viable long term treatment of diabetes.

The islets of Langerhans are clusters of differentiated cells sharing a common precursor. Found in the pancreas of mammals, islets taken together can be considered as a single endocrine organ. The islets occupy about 7% of the human pancreas which also contains the exocrine acinar tissue. The composition of cells in the islets differs depending on the location of the islet in the pancreas. Central to each islet is a core of insulin secreting beta cells. Surrounding the beta cells are somatostatin secreting delta cells, glucagon secreting alpha cells and pancreatic polypeptide containing f cells. Alpha cells tend to be concentrated in the tail and the body of the pancreas whereas, the f cells are concentrated in the head. This distribution corresponds to the embryonic origin of alpha and f cells from dorsal and ventral primordium of the pancreas.

Pancreatic beta cells are the only cells in which the insulin gene is expressed and, therefore, are the sole source of metabolic insulin in vertebrates. Insulin is necessary in maintaining glucose homeostasis and plays a role in the normal processing of proteins and fats. Insulin release can be inhibited by low levels of somatostatin and stimulated by glucagon. Without sufficient insulin to metabolize glucose, hyperglycemia occurs. Insulin-dependant diabetes mellitus is a direct result of nonfunctional islets, specifically beta cells.

Among the major obstacles in islet transplantation research is an inability to induce proliferation and to keep islets viable over time. Researchers have encountered many obstacles in attempting to cure diabetes resulting from the loss of islet function. For transplantation, it is necessary to preserve islet viability as well as gene expression and secretory function.

Pancreatic islets do not grow readily in primary cultures. However, these endocrine cells have been grown with difficulty as monolayers. This difficulty of long-term culture has not only hindered the laboratory research for such islets, but it has also hindered attempts to carry out physiological and even clinical studies with such islets. Therefore, there is needed a medium for the long-term proliferation of islets. A medium for the long-term survival of cells is additionally needed for other cell types.

Additionally, current methods of transplantation must suppress immune response by the host organism that may lead to rejection of the transplanted cells and loss of islet function. Thus, there is also a need in the art for a simple, non-invasive method of introducing hormone secreting cellular moieties, such as insulin secreting pancreatic islets, into a hormone deficient organism without requiring general immunosuppressive agents.

SUMMARY OF THE INVENTION

A cell culture medium to promote the proliferation and long-term survival of cells is provided. The cell culture medium includes elevated levels of polar amino acids. The addition of polar amino acids to the medium enhances cell proliferation and maintains cell viability for sustained periods of time.

Additionally, a hydrogel matrix for the long-term proliferation of cells is provided. The matrix includes elevated levels of polar amino acids. The matrix of the present invention may be used as a carrier for direct injection of cells into a host organism without significant loss of cell viability or function. Additionally, the matrix acts to shield the cells from the immune system of the host organism.

Also provided are transplants capable of long-term functioning in a host. In particular, insulin secreting transplants comprising islet cells and acinar cells are provided. The transplants of the present invention include the matrix and allows coexistence of islet and acinar cells with improved insulin pulsatility.

A cell culture medium for long term storage and proliferation of cells is provided. The cell culture medium includes an effective amount of polar amino acids. Preferred polar amino acids are selected from, but not limited to, the group consisting of arginine, lysine, histidine, glutamic acid, and aspartic acid. The effective amount of polar amino acids is preferably about 5 to about 150 mM and most preferably about 10 to about 64 mM. In one embodiment, the polar amino acids comprise about 2 to about 60 mM of arginine and about 2 to about 60 mM of L-glutamic acid. The cells cultured in the medium may be selected from a group consisting of lung cells, liver cells, kidney cells, thymus cells, thyroid cells, heart cells, brain cells, pancreatic islet cells, pancreatic acinar cells, and mixtures thereof.

A hydrogel matrix for long term storage and proliferation of cellular tissue is also provided, the matrix comprising about 0.01 to about 40 mM of gelatin and an effective amount of polar amino acids. The effective amount of polar amino acids is preferably from about 3 to about 150 mM and most preferably about 10 to about 65 mM. In one embodiment, the polar amino acids are selected from the group consisting of arginine, glutamic acid, lysine or mixtures thereof. Preferably, the hydrogel matrix includes about 2 to about 60 mM of L-glutamic acid, about 1.5 to about 10 mM of L-lysine and about 1 to about 40 mM of arginine.

A method of maintaining, cell viability and functioning during storage is provided wherein the cells are imbedded in the hydrogel matrix of the present invention. The matrix protects cells during storage, including frozen storage.

A method of maintaining viability and functioning of a transplant cell after introduction into a host organism is also provided. The method includes the steps of embedding the cells in the hydrogel matrix described above and injecting the embedded cells into the host organism. While the majority of the matrix liquifies and is absorbed by the host, polar moieties of the matrix attach to cell surface polar moieties, thus obscuring cell surface immune recognition proteins. Advantageously, the hydrogel matrix may be injected into a transplant site prior to injection of the cells to encourage vascularization. The encapsulated cells may be isolated from a different species than the host organism.

The matrix of the present invention may also be used to stimulate vascularization at a site in a host organism to treat conditions benefitted from an increased supply of blood. The method includes contacting the site with the matrix of the present invention wherein the matrix comprises an effective amount of polar amino acids.

A transplant for implanting in a host organism is also provided. The transplant comprises cells having outer surfaces encapsulated by a matrix comprising an effective amount of polar amino acids. The effective amount of polar amino acids may be about 3 to about 150 mM. These polar amino acids serve to enhance bonding of other polar moieties and further obscure immune recognition proteins in a host subject. Thus, cells embedded in this enhanced hydrogel matrix substantially escape host immune destruction.

A method for increasing insulin production in a transplant is also provided. Insulin production may be increased in a transplant by providing a mixture of acinar cells and islet cells and encapsulating that mixture in a matrix comprising an effective amount of polar amino acids to form a transplant. The transplant is then injected into a host organism. Preferably the mixture of acinar cells and islet cells comprises at least about 30% by volume acinar cells and most preferably about 60% by volume acinar cells.

A method of metabolically refeeding stored cells is also part of the present invention. Stored cells may be refed by providing a container of stored cells at room temperature and adding cell culture medium of the present invention to the container. The container of stored cells is then incubated for a period of time. Advantageously, the cell culture medium is added in an amount equal to about 10 to about 40 µl/ml of stored cells.

A method of protecting cells during isolation of the cells after enzymic digestion of cell tissue is also included in the present invention. The method includes the steps of collecting digestate from a digestion process and adding cell culture medium of the present invention to the digestate to protect cells during isolation.

BRIEF DESCRIPTION OF THE DRAWINGS

Figure 2:
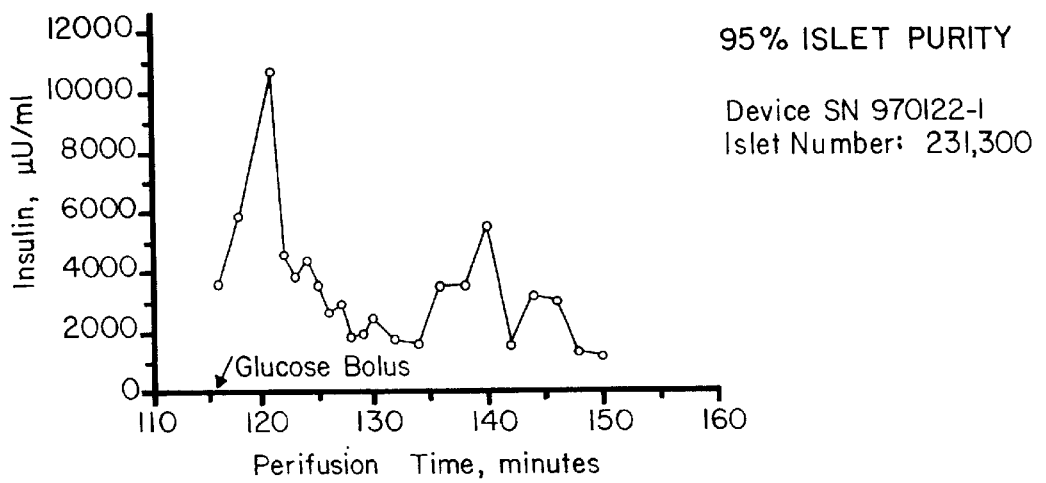
Figure 2:
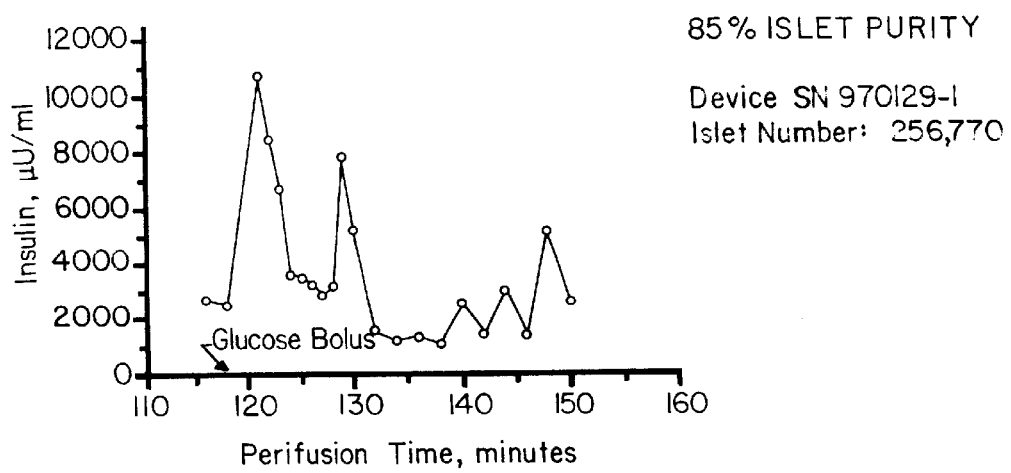
Figure 2:
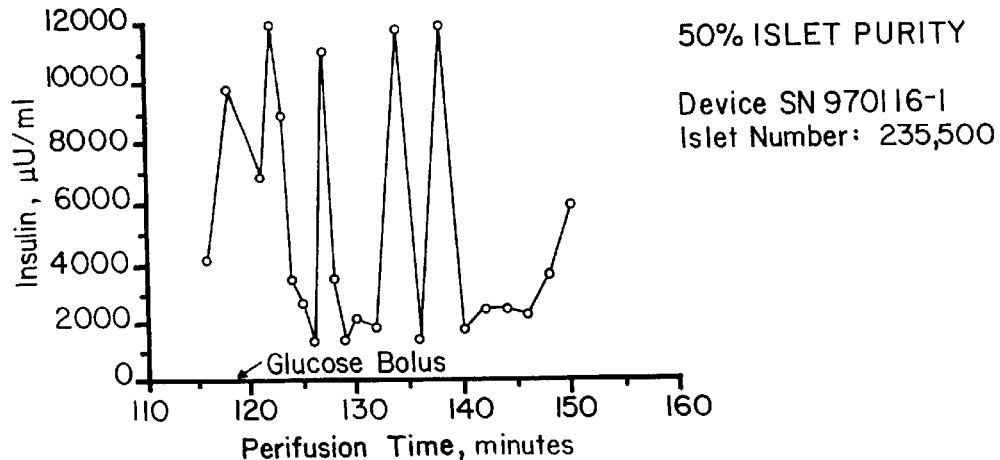

Having thus described the invention in general terms, reference will now be made to the accompanying drawings, wherein:

FIG. 1 is a table listing the amount of porcine c-peptide produced by three separately designated animals;

FIG. 2 is a set of three graphs indicating the relationship between insulin production and islet purity;

FIG. 3 is a table indicating insulin collection as a function of islet number, purity and age; and FIG. 4 is a bar chart showing the relationship between the blood glucose levels of two dogs.

DETAILED DESCRIPTION OF THE INVENTION

The invention comprises compositions and methods useful for making and using transplants. The invention also comprises compositions and methods of maintaining cell viability and function over long periods of time. Specifically, the invention provides a cell culture medium composition and matrix composition that facilitates long-term storage and transplantation of cells.

By transplant is intended cells, tissues, or other living or non-living devices for transplantation into a mammal. Transplants of the invention include allografts, artificial organs, cellular transplantation and other applications for hormone producing or tissue producing implantation into deficient individuals who suffer from conditions such as diabetes, thyroid deficiency, growth hormone deficiency, congenital adrenal hyperplasia, Parkinson's disease, and the like. Likewise, the matrix is useful for transplants involving therapeutic conditions benefitting from implantable delivery systems for biologically active and gene therapy, products for the treatment of central nervous system diseases and other chronic disorders. More specifically, the matrix as described will find application in the various transplantation therapies, including without limitation cells secreting human nerve growth factors for preventing the loss of degenerating cholinergic neurons, satellite cells for myocardial regeneration, striatal brain tissue for Huntington's disease, liver cells, bone marrow cells, dopamine-rich brain tissue and cells for Parkinson's disease, cholinergic-rich nervous system for Alzheimer's disease, adrenal chromaffin cells for delivering analgesics to the central nervous system, cultured epithelium for skin grafts, and cells releasing ciliary neurotropic factor for amyotrophic lateral sclerosis, and the like.

Cell Culture Medium

In order to cultivate animal cells in vitro, conditions such as those found in vivo must be reproduced as closely as possible. These conditions are affected by numerous factors, including: temperature, pH, osmotic pressure, cell growth matrix, essential metabolites, supplemental metabolites, hormones, and specific factors for cell metabolism such as transport factors, antibiotics, etc.

A medium for the long-term survival and proliferation of cells is provided. In general, the terms "medium" and "media" in connection with the present invention are solutions containing growth factors and nutrients which are used to support the growth and development of cells, particularly islet cells. By "long-term" is meant continuous growth and development of the cells being cultured, for a time period of at least about 12 to about 20 weeks, preferably greater than 20 weeks, and more preferably greater than 40 weeks.

The medium of the invention is useful for the growth and proliferation of a variety of cells. Such cells may be derived from a variety of tissues such as lung, liver, kidney, thymus, thyroid, heart, brain, pancreas, and the like.

A number of amino acids are included within the medium. Of particular interest are polar amino acids, particularly arginine and glutamic acid. By amino acid is intended all naturally occurring alpha amino acids in both their D and L stereoisomeric forms, and their analogues and derivatives. An analog is defined as a substitution of an atom in the amino acid with a different atom that usually has similar properties. A derivative is defined as an amino acid that has another molecule or atom attached to it. Derivatives would include, for example, acetylation of an amino group, amination of a carboxyl group, or oxidation of the sulfur residues of two cysteine materials to form cystine.

The addition of supplemental amounts of polar amino acids is an important feature of the cell culture medium of the present invention. While the invention is not bound by any particular mechanism, it is believed that the polar amino acids strengthen cellular membranes by binding to polar groups found on the cellular membrane surface. This increases the integrity of the cellular membrane and protects the cell from trauma in the culture medium environment. Additionally, the polar amino acids may bond to immune recognition sites on the cell surface which suppresses adverse immune responses.

The concentration of polar amino acids may be raised until an effective amount of polar amino acids are present in the culture medium. The preferred polar amino acids are selected from the group consisting of arginine, lysine, histidine, glutamic acid, and aspartic acid, although other chemicals containing polar amine and carbonyl groups may be used. An effective amount is the amount necessary to strengthen cellular membranes and bond to immune recognition sites on the cell surface. In one embodiment, the concentration of polar amino acids is raised to a final concentration of between about 5 to about 150 mM, preferably about 10 to about 65 mM, and more preferably about 15 to about 40 mM.

Advantageously, supplemental amounts of arginine and L-glutamic acid are added to the culture medium of the present invention. Preferably, the final concentration of arginine is About 2 to about 60 mM, preferably about 5 to about 30 mM, most preferably about 5 to about 15 mM. The final concentration of L-glutamic acid is about 2 to about 60 mM, preferably about 5 to about 30 mM, most preferably about 10 to about 20 mM. In one embodiment, the final concentration of arginine is about 10 mM and the final concentration of L-glutamic acid is about 15 mM.

The cell culture medium may also be used to protect cells during an isolation process following digestion of cellular tissue. By adding the cell culture medium to the digestate, the cells are protected from digestion, the mechanical trauma caused by the isolation process, and later, after mixing with serum, attack by high affinity antibodies. The result is less cell fragmentation during isolation.

In addition to supplemental amounts of polar amino acids, the culture medium of the present invention also comprises a standard culture medium supplemented with a buffering agent, salt solution and other additives. The preferred standard culture medium is Medium 199 1xliquid. However, other standard culture media known in the art would be suitable for use with the present invention. Standard culture media which may be employed in accordance with the present invention are standard culture media for growing cells that typically provide an energy source, such as glucose, substantially all essential and nonessential amino acids and vitamins and/or other cell growth supporting organic compounds required at low concentrations. When combined with a buffering agent and a salt solution, the standard culture medium provides many of the nutrients required for normal metabolic functioning of cultured cells.

The preferred salt solution is Earle's Balanced Salts. The salt solution helps to maintain pH and osmotic pressure and also provides a source of energy. The preferred buffering agent is Hepes. Other salt solutions and buffering agents known in the art may be used without departing from the present invention.

Table 1 below lists the particularly preferred components along with preferred approximate concentrations for each component of a solution containing a standard culture medium, buffering agent and salt solution. The concentrations are based on use of Medium 199 liquid, Earle's Balanced Salts and Hepes.

TABLE 1

| Component | Preferred Concentration (mM) |
|---|---|
| Inorganic Salts | |
| Calcium Chloride | 1.26000 |
| potassium chloride | 5.34000 |
| potassium phosphate | 0.43900 |
| Magnesium sulfate * 7H20 | 0.83074 |
| Sodium chloride | 90.48920 |
| sodium bicarbonate | 4.14050 |
| sodium phosphate | 0.38500 |
| ferric nitrate *9H20 | 0.00170 |
| sodium acetate | 0.62000 |
| Amino Acids | |
| Cystine | 0.08300 |
| L-alanine | 0.11670 |
| L-arginine HCl | 0.39861 |
| L-aspartic acid | 0.23000 |
| L-cysteine HCl *2H20 | 0.00057 |
| L-glutamic acid | 0.51000 |
| L-glutamine | 0.68400 |
| glycine | 0.53674 |
| L-histidine HCl H20 | 0.12935 |
| L-hydroxyproline | 0.07600 |
| L-isoleucine | 0.33957 |
| L-leucine | 0.58299 |
| L-lysine HCl | 0.52630 |
| L-methionine | 0.07424 |
| L-phenylanine | 0.17424 |
| L-proline | 0.34497 |
| L-serine | 0.28878 |
| L-threonine | 0.08936 |
| L-tryptophan | 0.05860 |
| L-tyrosine 2Na*H20 | 0.44372 |
| L-valine | 0.09974 |
| Vitamins | |
| ascorbic acid (vitamin C) | 0.00233 |
| alpha-tocopherol phosphate | 0.00003 |
| d-biotin | 0.00004 |
| Dexpanthenol | 0.00008 |
| choline chloride | 0.00360 |
| folic acid | 0.00002 |
| i-inositol | 0.00028 |
| menadione | 0.00006 |
| niacin | 0.00024 |
| niacinamide | 0.00034 |
| para-aminobenzoic acid | 0.00036 |
| pyridoxal HCl | 0.00015 |
| pyridoxine HCl | 0.00023 |
| riboflavin | 0.00003 |
| Vitamin A acetate (retinol) | 0.00059 |
| Vitamin D (calciferol (ergo) | 0.00054 |
| Other Additives | |
| D-glucose | 4.15900 |
| adenine sulfate | 0.04300 |
| adenosine 5-triphosphate | 0.00190 |
| adenosine 5-phosphate | 0.00073 |
| cholesterol | 0.00052 |
| deoxyribose | 0.00370 |
| glutathione | 0.00016 |
| guanine HCl | 0.00160 |
| HEPES | 25.00000 |
| hypoxanthine sodium | 0.00290 |
| D-ribose | 0.00330 |
| thymine | 0.00240 |
| tween 80 | 0.01500 |
| uracil | 0.00240 |
| xanthine Na | 0.00034 |

Advantageously, aminoguanidine may be added to the cell culture medium of the present invention. Aminoguanidine is an L-arginine analogue and acts as a nitric oxide inhibitor. Nitric oxide and its metabolites are known to cause cellular death from nuclear destruction and related injuries. Other L-arginine analogues, such as N-monomethyl L-arginine, N-nitro-L-arginine or D-arginine could also be used in the present invention. Aminoguanidine is provided at a concentration of about 15 to about 250 μM, preferably about 30 to about 180 μM, most preferably about 80 to about 120 μM. In one embodiment, the concentration of aminoguanidine is about 100 μM.

The concentration of L-cysteine is also increased in the cell culture medium of the present invention. L-cysteine acts as a scavenger of already formed nitric oxide and thereby prevents nitric oxide induced cellular damage. Additionally, L-cysteine may obscure immune recognition sites on the cultured cells by sulfhydryl bond formation to integral surface proteins containing sulfur groups. Further, L-cysteine provides sulfhydryl bonds which strengthen cell membranes. The preferred final concentration of L-cysteine is about 50 to about 300 μM, preferably about 80 to about 250 μM, most preferably about 150 to about 200 μM. In one embodiment, the final concentration is about 180 μM.

Although it is possible to use the cell culture medium of the present invention as a serum-free medium, albumin or other nutrient sources may be added. Use of albumin instead of conventional sera reduces cost and facilitates transplantation of cells. It is recognized that any source of albumin may be used and generally human albumin is used in most conventional culture media. For purposes of the present invention, the albumin or serum used is preferably isolated from the same species as the cells to be stored in the culture medium. For instance, for culturing of porcine pancreatic islet cells, porcine albumin or serum would be used. Use of albumin from the same species as the cultured cells negates the problems of cross-species antibody attacks upon the cells and IgM cross-linking. The cultured cells are more robust when same-species sera is used. Preferably, the concentration of albumin is about 5 to about 50 μl/ml, preferably about 10 to about 30 μl/ml, most preferably about 15 μl/ml to about 25 μl/ml. In one embodiment, the concentration of albumin is about 20 μl/ml.

Other additives known in the art may also be added to the culture medium without departing from the present invention. For instance, antibiotics are preferably added to the medium. Any antibiotic known in the art may be used. It is recognized that the antibiotic of choice may vary depending on the type of cells. Preferred antibiotics include Coly-mycin, Amphotericin b, Ciprofloxacin and Gentamicin Sulfate and the like. The cell culture medium may also be supplemented with additional L-glutamine to compensate for the degradation of that amino acid that may occur over time.

Table 2 below lists the particularly preferred additives and supplemented ingredients for the culture medium of the present invention and summarizes the final concentration ranges and preferred final concentrations for each ingredient.

TABLE 2

| Components | Concentration Range | Preferred Concentration |
|---|---|---|
| Albumin | 5–50 μl/ml | 20 μl/ml |
| L-Cysteine HCl | 50–300 μM | 180 μM |
| Aminoguanidine | 15–250 μM | 100 μM |
| Coly-Mycin | 5–20 μg/ml | 10 μg/ml |
| Amphotericin B | 2–6 μM | 3.382 μM |
| Ciprofloxacin | 2–6 μg/ml | 5 μg/ml |
| Gentamicin Sulfate | 2–6 μg/ml | 4.8 μg/ml |
| L-Glutamine | 5–15 μM | 10 μM |

TABLE 2-continued

| Components | Concentration Range | Preferred Concentration |
|---|---|---|
| L-Glutamic Acid | 2–60 mM | 15 mM |
| Arginine HCl | 2–60 mM | 10 mM |

Matrix

The present invention also provides a hydrogel matrix for storage and transplantation of cells. The matrix is suitable for use with a variety of cells including cells derived from tissue of the lung, liver, kidney, thymus, thyroid, heart, brain, pancreas, and the like. The matrix of the present invention provides numerous advantages over matrixes of the prior art. The matrix of the present invention is able to sustain cells and complex clusters of cells such as islets. One advantage of the matrix is its ability to immobilize water at appropriate storage temperatures and provide binding sites for cells that apparently stimulate growth in terminal cell types, such as beta cells.

The matrix of the present invention also contains materials that provide scaffolding for both cellular attachment and protection. This attribute of the matrix obviates the need for sera in maintaining long term cell cultures, such as long term cultures of islets, pancreatic acinar tissue, hepatocytes, and erythrocytes. The matrix may be mixed with cells to form a transplant for injection into a host organism at a transplant site without the use of an additional protective carrier device. Transplant site is intended to mean the predetermined site where the transplant will be placed within the host organism. In this manner, the matrix allows transplantation of cells through a non-invasive and simple procedure.

A surprising feature of the matrix of the present invention is that use of the matrix allows transplantation of pancreatic islet cells at lower purity levels. Conventionally, islet cells are utilized at high purity levels to avoid substantial amounts of acinar cells in contact with the islet cells because of digestion of the islet cells by the acinar cells' digestive enzymes. This results in very costly and time consuming purification methods, as well as disposal of most pancreatic tissue because of the presence of acinar tissue. The matrix of the present invention allows coexistence of acinar cells with islet cells in vitro and after transplantation in the host organism. The matrix allows the use of cell mixtures containing as much as 70% by volume or more of acinar cells. It is believed that the optimum range is about 30 to about 40% by volume islet purity.

The unpurified pancreatic tissue also functions better than purified islet cells. Unpurified pancreatic tissue has been shown to exhibit insulin pulsatility that more closely simulates the insulin pulsatility seen in the normal functioning of pancreatic tissue of a non-diabetic organism. The advantage of using unpurified cells is their ability to mimic normal pancreatic functions, such as insulin pulsatility. The insulin pulsatility of normally functioning pancreatic tissue is characterized by peak concentrations occurring every 5–10 minutes.

Another feature of the matrix is its ability to stimulate or enhance vascularization in surrounding tissue. Vascularization refers to the formation of blood vessels. Stimulation or enhancement of vascularization is defined as increasing blood vessel formation and resulting blood circulation beyond that which would occur naturally. Due to the vascularization effect, an effective amount of the matrix may be applied to a transplant site prior to the transplant. An effective amount is an amount necessary to stimulate the flow of blood to the transplant site. In this manner, the matrix improves vascularization at the transplant site so that a blood supply is already available for the cells when the transplant occurs. However, matrix is routinely applied to the transplant site at the time of the procedure with neovascularization occurring within 4 to 7 days. The vascularization effect of the matrix increases the likelihood of long-term cell viability in a host organism.

It is also recognized that the matrix may be used to treat conditions benefitted by increased vascularization. Such conditions include those which would benefit from an increased supply of blood such as gangrene, wound sites, and general poor circulation problems. Additionally, formation of new blood vessels in the heart is critically important in protecting the myocardium from the consequences of coronary obstruction. Injection of the matrix into ischemic myocardium may enhance the development of collaterals, accelerate the healing of necrotic tissue and prevent infarct expansion and cardiac dilatation.

The matrix is suitable for use in the transplantation of cells within a transplant device such as described in U.S. patent application Ser. No. 08/568,694, which is herein incorporated by reference in its entirety. A transplant device is any device designed to contain and protect cells transplanted into a host organism for the production of hormones or other factors. Examples of other transplant devices suitable for use with the matrix include those described in U.S. Pat. Nos. 5,686,091, 5,676,943 and 5,550,050. However, as discussed above, the matrix may be used as the sole transplant vehicle without using such devices.

The matrix also finds use in storage of cells without loss of viability or specialized cell function. For long term storage, cells may be frozen in the matrix without significant loss of viability. This has application in shipping blood cells, hepatocytes, pancreatic tissue, hemopoietic stem cells, bone marrow, Leydig cells, thyroid cells, pituitary cells, cardiac cells, renal cells, and others either alone or in combination, for clinical or research applications.

Current blood banking techniques allow erythrocytes to be stored for only two months. The matrix of the present invention allows erythrocytes to remain morphologically intact for seven months. The matrix has also been demonstrated to maintain the highly specialized function of cells for extended periods of time. Hepatocytes have maintained their specialized thiol transferase, albumin, and cytochrome p450 enzymes for up to 8 weeks in vitro when stored in the matrix. Drug metabolizing activity has been maintained for at least two weeks during storage of hepatocytes in matrix. Human red blood cells have been stored for over 8 months and reconstituted by adding water without cellular lysis. A human neuron cell line has been demonstrated to keep specific message for up to 4 weeks. The matrix thus appears to be able to keep a variety of partially or totally isolated cells alive and functional for extended periods of time.

An important feature of the matrix of the present invention is the increased level of polar amino acid groups. The addition of polar amino acids increases the number of hydrogen bonding moieties which subsequently increase the rigidity of the matrix. The increased hydrogen bonding attracts and immobilizes water. This immobilization of water reduces cell membrane damage caused by temperature changes. It is also believed that the polar amino acid groups contribute to molecular encapsulation of the cells therein and block the immune recognition sites present on the cell surface. This characteristic allows cells stored in the matrix to be directly injected into a host organism without recognition by the host organism's immune system that the injected cells are foreign. This would allow cross-species transplantation of cells without immunosuppression. For example, porcine pancreatic islet cells could be injected into human hosts using the matrix of the present invention. Use of the matrix of the present invention obviates the need for additional protective measures to prevent a negative immune system response by the host organism.

The matrix may contain an effective amount of polar amino acids therein. The polar amino acids may be selected from the group consisting of arginine, lysine, histidine, glutamic acid, and aspartic acid, or other amino acids or other polar chemicals. An effective amount is the amount necessary to increase the rigidity of the matrix and allow direct injection of the matrix with cells encapsulated therein into a host organism without immunosuppression. In one embodiment, the concentration of polar amino acids is raised to a final concentration of between about 3 to about 150 mM, preferably about 10 to about 65 mM, and more preferably about 15 to about 40 mM.

Advantageously, the added polar amino acids comprise L-glutamic acid, L-lysine, and arginine. The final concentration of L-glutamic acid is about 2 to about 60 mM, preferably about 5 to about 40 mM, most preferably about 10 to about 20 mM. In one embodiment, the concentration of L-glutamic acid is about 15 mM. The final concentration of L-lysine is about 0.5 to about 30 mM, preferably about 1 to about 15 mM, most preferably about 1 to about 10 mM. In one embodiment, the concentration of L-lysine is about 5.0 mM. The final concentration of arginine is about 1 to about 40 mM, preferably about 1 to about 30, most preferably about 5 to about 15 mM. In one embodiment, the final concentration of arginine is about 10 mM.

The matrix of the present invention is a combination of a gelatin component and a liquid composition. The gelatin acts as a substrate for cellular attachment. The preferred gelatin component is denatured collagen. Denatured collagen contains polar and non-polar amino acids that readily form a gel based on amine, carboxyl group, hydroxyl group, and sulfhydryl group interactions. The matrix is designed to be in a free flowing or liquid phase at host body temperature in order to provide maximum diffusion across the membrane in vivo. The matrix remains in solid phase at the lower storage temperatures, such as 4° C.

Boiling or otherwise treating intact collagen to form denatured collagen breaks covalent chemical bonds and increases the number of heat sensitive hydrogen bonds and dipole moment attractions. By replacing the covalent chemical bonds with temperature sensitive bonds and attractions, the desired cells can be embedded in a solid matrix formulation at colder temperatures for sustained storage. Boiling or otherwise treating intact collagen breaks the tightly coiled helical tropocollagen subunits and causes the subunits to open up into separate peptide chains. These uncoiled strands provide multiple binding areas for cells to attach.

The gelatin is present at a concentration of about 0.01 to about 40 mM, preferably about 0.05 to about 30 mM, most preferably about 1 to 5 mM. Advantageously, the gelatin concentration is approximately 1.6 mM. The above concentrations provide a solid phase at storage temperature and a liquid phase at transplant temperature.

The gelatin component of the matrix of the present invention is mixed with a liquid composition. The liquid composition is preferably based upon a standard culture medium, such as Medium 199, supplemented with additives and additional amounts of some medium components, such as supplemental amounts of polar amino acids as described above.

An additional amount of L-cysteine may be added to the matrix of the present invention. L-cysteine acts as a nitric oxide scavenger and obscures immune recognition sites on the surface of the cells. L-cysteine also provides disulfide linkages which increases the matrix's resistance to force and further protects the cells contained therein. The final concentration of L-cysteine is about 5 to about 500 μM, preferably about 10 to about 100 μM, most preferably about 15 to about 25 μM. In one embodiment, the final concentration is about 20 μM.

Advantageously, aminoguanidine is also added to the matrix of the present invention. As indicated above, aminoguanidine is an L-arginine analogue and acts as a nitric oxide inhibitor. Other L-arginine analogues could also be used in the present invention. The final concentration of aminoguanidine is about 5 to about 500 μM, preferably about 10 to about 100 μM, most preferably about 15 to about 25 μM. In one embodiment, the final concentration is about 20 μM.

In order to increase cell binding, intact collagen may be added in small amounts to provide an additional binding network for the cells contained in the matrix. The final concentration of intact collagen is from about 0 to about 5 mM, preferably 0 to about 2 mM, most preferably about 0.05 to about 0.5 mM. In one embodiment, the concentration of intact collagen is about 0.11 mM.

Additionally, the matrix to the present invention may include a divalent chelator which increases the rigidity of the matrix by removing inhibition of —NH$_2$ to —COOH hydrogen bonding. The divalent chelator also protects against microbial contamination of the matrix. A preferred divalent chelator is EDTA. The concentration range for the chelator is about 0 to about 10 mM, preferably 1 to about 8 mM, most preferably about 2 to about 6 mM. In a preferred embodiment, EDTA is present at a concentration of about 4 mM. Conventional antibiotics can also be added to further protect against microbial contamination.

As indicated above, the matrix of the present invention does not require the presence of sera in order to maintain long term cell cultures. However, albumin or other nutrient sources may be added to the matrix of the present invention if desired. Preferably, the albumin used is of the same species as the cells contained within the matrix. As described above, use of the same species albumin promotes increased robustness in the cells contained in the matrix. The concentration of albumin is about 0 to about 2% by volume, preferably 0 to about 0.5% by volume, most preferably about 0 to about 0.1% by volume. In a preferred embodiment, the concentration of albumin is about 0.05 % by volume.

The addition of high concentrations of polar amino acid enhancements, or other polar substrates, further improves the immobilization of water such that cells or cell combinations may be frozen to at least −20° C. without apparent morphologic or functional damage. The increased concentrations of L-glutamic acid, L-lysine, arginine, in addition to increased concentrations of cysteine, result in increased denatured connective tissue immobilization of water at cold temperatures. Thus, the current invention demonstrates a long term cryopreservation ability without the use of membrane solubilizing agents such as DMSO (Dimethyl Sulfoxide) that are commonly used to cryopreserve isolated cells.

For long term storage, an effective amount of cryoprotectant may be added that allows the matrix to be stored at lower temperatures without cellular damage. Preferably, the cryoprotectant is metabolically stable and capable of creating an inert cushion to prevent thermal expansion and contraction of cells. A preferred cryoprotectant is sulfated dextran. The cryoprotectant is present at a concentration of about 0 to about 2 mM, preferably 0 to about 1 mM, most preferably about 0 to about 0.1 mM. In one embodiment, the cryoprotectant is present in a concentration of about 0.086 mM.

Table 3 below lists particularly preferred key components of the matrix of the present invention along with suitable concentrations as well as preferred concentrations for each component.

TABLE 3

| Component | Concentration Range | Preferred Concentration |
|---|---|---|
| L-glutamic acid | 2 to 60 mM | 15 mM |
| L-lysine | .5 to 30 mM | 5.0 mM |
| Arginine | 1 to 40 | 10 mM |
| Gelatin | 0.01 to 40 mM | 1.6 mM |
| L-cysteine | 5 to 500 μM | 20 μM |
| Aminoguanidine | 5 to 500 μM | 20 μM |
| Intact collagen | 0 to 5 mM | 0.11 mM |
| EDTA | 0 to 10 mM | 4 mM |
| Albumin | 0 to 2 % by volume | 0.05 % by volume |
| Dextran | 0 to 2 mM | 0.086 mM |

Matrix Preparation

Place 835 ml of Medium 199 into a stirred beaker. While stirring, heat the solution to 50° C. Using a syringe, add 20 ml of albumin to the stirred solution. Pipette 63.28 μl of cysteine, 1 ml of L-glutamine and 200 μl of aminoguanidine into the stirred beaker. Add the following gamma irradiated dry raw materials: 120 grams of denatured collagen, 50 grams of dextran, and 0.1 grams of intact collagen. Use a glass stirring rod to aid mixing of the dry materials into solution. Pipette 8 ml of EDTA into the solution. Pipette 5 ml of L-glutamic acid, 5 ml of L-lysine acetate, and 5 ml of arginine HCl into the stirred beaker. Note that the solution will turn yellow. Use 10% NaOH to adjust the pH of the matrix solution to a final pH of 7.40±0.05.

Cells may be embedded in the matrix of the present invention using the following procedure. Aspirate the supernatant from centrifuged cell pellets. Add a volume of cell culture medium and matrix to the cell pellets. Add a volume of matrix approximately equal to about 4 times the pellet volume. Add a volume of cell culture medium to the cell pellets equaling approximately 0.05 times the matrix volume added. Store the encapsulated cells at refrigerated temperatures if not using immediately.

The present invention also provides a method of refeeding cells stored in the matrix of the present invention. Conventionally, cell cultures could not be maintained for a duration long enough to require refeeding of the cells. However, using the matrix of the present invention, cell viability may be maintained for longer periods of time, necessitating periodic refeeding of the cells. Additionally, bringing the cells to room temperature periodically allows evaluation of cell function and viability and encourages the development of communication networks, between cells.

Periodically, during refrigeration of the cell/matrix mixture, the cells may be refed or metabolically "walked" using the following procedure. First the stored cell/matrix mixture is retrieved from refrigeration. The mixture is examined for excess fluid. If excess fluid is present, the fluid is pipetted away and discarded. Cell culture medium is then added to the mixture. In one embodiment, 400 μl of the cell culture medium of the present invention is pipetted into each 15 ml container of the cell/matrix mixture. The container is shaken to distribute the cell culture medium over the entire cell/matrix mixture. The container is then capped and transferred to a 37° C. incubator. The containers are incubated for about two hours and then transferred back to refrigeration.

The following examples are offered by way of illustration and not by way of limitation.

EXPERIMENTAL

Example 1

The bottom of FIG. 1 lists the amount of porcine c-peptide in ng/ml per week produced by a rabbit designated Rabbit 6. Rabbit 6 was part of a study that utilized a bioartificial endocrine device containing porcine islets in the matrix of the present invention. The bioartificial device was taken out after 7 weeks, designated "Week O". At that time the device was surgically removed, and it was discovered that the device had ruptured resulting in the porcine islets and matrix leaking into the surrounding tissue of Rabbit 6. However, as indicated in FIG. 1, Rabbit 6 continued to produce detectable levels of porcine c-peptide until week 27. This suggests that the porcine islets in the matrix of the present invention produced a well vascularized, immunoprivileged site within the tissue of the rabbit.

Example 2

Also referring to FIG. 1, a rabbit designated as Rabbit 3 was injected with 3 ml of unpurified pancreatic tissue (7% islet tissue) and 2.6 ml of purified islet tissue (100% purity). Four weeks after the injection, the rabbit displayed a significant concentration of porcine c-peptide and achieved levels of up to 0.3 ng/ml during IV glucose tolerance testing 6 weeks after the injection. The rabbit continued to produce porcine c-peptide for 13 weeks after the injection. This indicates that unpurified, pancreatic tissue functions effectively in vivo.

Example 3

Referring again to FIG. 1, a non-diabetic dog was injected with unpurified islets (dog 22136). After injection, the dog produced 0.2 ng/ml porcine c-peptide within 6 days of implant and demonstrated levels of at least 0.1 ng/ml porcine c-peptide at all 15 blood draw points during a 90 minute IV glucose tolerance test. Two other dogs were injected with partially purified islets. Those two dogs demonstrated 0.1 ng/ml on one occasion each after 4 weeks.

This supports a finding that unpurified pancreatic tissue, after being placed in the matrix of the present invention, produces mature insulin product as measured by c-peptide much sooner and in much greater quantity per islet than purified islets. This is an unexpected finding because previous findings indicated that islet transplantation required use of substantially purified islets to prevent digestion of the islets by the acinar cells. However, using the matrix of the present invention, islets coexist with acinar cells without negative effect and appear to regain physiological function faster, both in terms of quantity produced and insulin pulsatility.

Example 4

Referring to FIG. 2, three semipermeable devices consisting of the same number of porcine islets in enhanced matrix (containing polar amino acids), but differing amounts of acinar tissue were perfused for 115 minutes at 37° C. with a physiologic buffer containing 100 mg/dl glucose. At 115 minutes, a bolus of glucose was injected into the solution to bring the total glucose concentration up to 300 mg/dl for a period of 40–60 minutes post-bolus.

The highly purified islet device (95% islet purity) released 11,000 uU insulin/ml within 5 minutes of seeing the glucose bolus, but only had one much smaller insulin peak of 5000 uU insulin/ml about 25 minutes later. Slightly less purified material (85% islet purity) demonstrated the same initial peak of insulin at 5 minutes post bolus of 11,000 uU insulin/ml, but showed another peak of 8,000 uU insulin/ml 15 minutes post bolus, followed by small pulsations 25–45 minutes post bolus. In the device containing only 50% islets, there were 4 peaks over a 22 minute period of between 11,000 and 12,000 uU insulin/ml demonstrating physiologic insulin pulsatility. These data demonstrate the ability of the matrix to sustain partially purified pancreatic tissue and allow such tissue to function physiologically.

Example 5

FIG. 3 illustrates the amount of insulin collected as a function of number of islets, purity and age. With 38% purity, over two hours with only 9.2 thousand islets, 3,550,000 uU insulin (or 3.65 units) were produced. When the number of islets were doubled to 18.4 thousand islets, the total insulin doubled to 8,400,000 uU insulin produced in 2 hours. Similar results, though slightly lower, were obtained from islets of only 31% purity. Of note is the extremely small volume of tissue in the matrix required to produce such large amounts of insulin—only 0.2 or 0.4 ml. The apparent optimal range is from about 30 to about 40% islet purity.

The matrix thus has been demonstrated to improve the communication among different cell types that apparently results in a substantial improvement of function. Thus the matrix not only protects the cells from physical and immunologic trauma, it also facilitates cellular communication in vitro so that the cells can maintain their function as seen in vivo.

Example 6

Two canine subjects were pancreatectomized within two weeks of each other and were treated with injections of mixtures of Ultralente and Regular insulin twice daily. Both animals were fed identical amounts of food with Viokase added to replace pancreatic digestive enzymes. Blood glucose values were determined in the morning and late afternoon, and exogenous insulin requirements were based on these values.

For four weeks prior to one of the dogs being injected with 8 cc of one volume unpurified pancreatic tissue per four volumes matrix, the two dogs had statistically equivalent blood glucose determinations, and received the same dose of insulin twice daily. The blood glucose levels of a dog that was not injected (darkly shaded line) and a dog that was ultimately injected intramuscularly on Day 0 (lightly shaded line) are shown in FIG. 4. The daily AM and PM blood glucose determinations are shown beginning one week prior to injection, and out for a total of three weeks (22 days).

FIG. 4 demonstrates that there was no statistical difference in the AM or PM blood glucose determinations during the week prior to one dog receiving the porcine tissue injection. Beginning the day of injection, the injected dog had a statistically significant decrease in the PM blood glucose on the same insulin dose as the uninjected dog. There was no statistical difference in the AM blood glucose during the first week after injection, probably reflecting the increased insulin resistance that mammals experience in the morning due to the effects of counter regulatory hormones such as cortisol and growth hormone. Type I diabetics generally require twice as much insulin in the AM to cover the same ingestion of carbohydrates as they require pre-supper because of this AM "cortisol" effect.

Beginning seven days after the injection, blood glucose levels in the injected dog clearly separated from those of the uninjected animal. Both animals had their insulin decreased 15% beginning week two. The injected dog's glucose continued to normalize, while the uninjected dog's blood glucose rose as expected. The injected animal continued to have statistically significant decreased blood glucose compared to the uninjected animal over the three week period. At that point, we separated the animals' insulin dose so that the uninjected dog could be better controlled.

Example 7

The uninjected animal in Example 6 was injected with unpurified porcine pancreatic material embedded in the matrix of the present invention to further protect the cells from immune recognition. Approximately 8 cc of this material was injected intramuscularly into the previously uninjected dog.

Beginning that evening, the dog's blood glucose fell, and the total insulin dose was cut 33%. The dog went at least seven days with the change in daily mean blood glucose and daily mean insulin dose shown below:

TABLE 4

|  | Mean Daily Blood Glucose | Mean total daily insulin dose |
| --- | --- | --- |
| Seven days prior to injection | 180 mg % | 64 units |
| Seven days post injection | 101 mg % | 43 units |

These data demonstrate that the injected porcine tissue has the effect of more than 20 units of exogenously administered insulin, since the average blood glucose has fallen nearly 40% and normalized on 20 units less insulin. The total daily insulin released in the average human subject is approximately 0.25 units/kg body weight, or 20 units per day in an 80 kg man. These data do not necessarily reflect 20 units of insulin production, since the pulsatile release of the pancreatic tissue probably increases the animal's insulin sensitivity.

These data clearly show the ability of unpurified porcine pancreatic tissue to function without the use of immunosuppression. Based on the above figures, isolated cells from three pancreases could treat 30–50 patients.

Example 8

Islet beta cells in the matrix of the present invention were observed after 7 days at 4° C. in the presence of a large acinar cell with digestive granules present. The cells appeared to have normal cytoplasm and intact ultrastructure, compared to pancreatic cells kept in Medium 199 under the same conditions. The islet cells in Medium 199 showed their cytoplasm washed out with the acinar cell releasing digestive enzyme material.

Example 9

Porcine liver was digested by dicing the organ into small slices, and placing the material in collagenase for five minutes. The digested hepatocytes, Kupfer cells, and epithelial cells were then placed in the above matrix and kept for 10 days at 4° C. Trypan blue exclusion stain revealed 90% viability at 10 days. In another experiment, gene expression for albumin was measured in 77 day old cells and lidocaine metabolism measured in 13 day old porcine hepatocytes in matrix of the present invention.

Example 10

Fresh whole blood from an adult male donor was centrifuged, and serum removed. The cellular pellet was divided into two 1 ml aliquots, and placed in either 4 ml Hanks Buffered Saline Solution or the above matrix, and stored at 4° C. for seven months.

At the end of seven months, the cells stored in the Hanks Solution had totally lysed, with no cells seen under 100× light microscopy. The matrix-containing cellular pellet was heated to 37° C., and diluted 1:1 with Hanks Solution. Intact erythrocytes with biconcave morphology at 100× light microscopy were present in the matrix-containing pellet.

Example 11

Unpurified and purified porcine pancreatic tissue was digested from fresh pancreata using standard collagenase digestion techniques. The unpurified or gradient purified samples were placed in a matrix containing 5 mM lysine, 5 mM arginine, and 10 mM glutamic acid, in addition to 180 μM cysteine, in a one part tissue volume to four parts matrix volume, placed in polypropylene tubes, and stored from 1 day to 6 weeks at −20° C. The previously frozen tissue was then thawed and stained with TSQ (N-6-methyl-8-quinolyl paratoluenesulfonamide), a flourescent zinc dye that indicates intracellular presence of insulin.

Inspection of the cells indicated appropriate morphology of both the islet tissue and digestive acinar cells in an unpurified preparation that was frozen for 6 weeks.

Many modifications and other embodiments of the invention will come to mind to one skilled in the art to which this invention pertains having the benefit of the teachings presented in the foregoing descriptions and associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for increasing insulin production in a transplant, said method comprising:

providing pancreatic tissue comprising islet cells and at least about 30% by volume acinar cells;

encapsulating the pancreatic tissue in a matrix comprising gelatin and an effective amount of polar amino acids to form a transplant, said polar amino acids selected from the group consisting of arginine, lysine, histidine, glutamic acid, and aspartic acid; and introducing the transplant into a host organism.

2. A method according to claim 1, wherein the pancreatic tissue comprises at least about 60% by volume acinar cells.

3. A method according to claim 1, wherein the matrix comprises about 0.01 to about 40 mM gelatin.

4. A method according to claim 1, wherein the effective amount of polar amino acids comprises about 3 to about 150 mM of polar amino acids.

5. A method according to claim 1, wherein the effective amount of polar amino acids comprises about 10 to about 65 mM of polar amino acids.

6. A method according to claim 1, wherein the polar amino acids are selected from the group consisting of arginine, glutamic acid, lysine and mixtures thereof.

7. A method according to claim 6, wherein the matrix comprises:
- about 2 to about 60 mM of L-glutamic acid;
- about 0.5 to about 30 mM of L-lysine; and
- about 1 to about 40 mM of arginine.

8. A method according to claim 7, wherein the matrix comprises:
- about 5 to about 40 mM of L-glutamic acid;
- about 1 to about 15 mM of L-lysine; and
- about 1 to about 30 mM of arginine.

9. A method according to claim 1, wherein the matrix further comprises about 5 to about 500 $\mu$M of L-cysteine.

10. A method according to claim 9, wherein the matrix comprises about 15 to about 25 $\mu$M of L-cysteine.

11. A method according to claim 1, wherein the matrix further comprises about 5 to about 500 $\mu$M of an L-arginine analogue.

12. A method according to claim 11, wherein the matrix comprises about 15 to about 25 $\mu$M of an L-arginine analogue.

13. A method according to claim 11, wherein the L-arginine analogue comprises aminoguanidine.

14. A method according to claim 1, wherein the effective amount of polar amino acids comprises about 10 to about 20 mM of L-glutamic acid.

15. A method according to claim 1, wherein the effective amount of polar amino acids comprises about 5 to about 15 mM of arginine.

16. A method according to claim 1, wherein the effective amount of polar amino acids comprises about 1 to about 10 mM of L-lysine.

17. A method according to claim 1, wherein the matrix further comprises about 1 to about 8 mM of a divalent chelator.

18. A method according to claim 17, wherein the divalent chelator comprises EDTA.

19. A method according to claim 1, wherein the matrix further comprises a long chain carbohydrate.

20. A method according to claim 19, wherein the long chain carbohydrate comprises dextran.

21. A method according to claim 1, wherein the matrix further comprises about 0.05 to about 0.5 mM of intact collagen.

22. A method according to claim 1, wherein the gelatin comprises denatured collagen.

23. A method according to claim 1, wherein said introducing step comprises injecting the transplant into a host organism.

24. A method for increasing insulin production in a transplant, said method comprising:
- providing pancreatic tissue comprising islet cells and at least about 30% by volume acinar cells;
- encapsulating the pancreatic tissue in a matrix comprising denatured collagen, dextran, an L-arginine analogue and an effective amount of polar amino acids to form a transplant, said polar amino acids selected from the group consisting of arginine, lysine, histidine, glutamic acid, and aspartic acid; and
- introducing the transplant into a host organism.

25. A method according to claim 24, wherein the pancreatic tissue comprises at least about 60% by volume acinar cells.

26. A method according to claim 24, wherein the matrix comprises about 0.01 to about 40 mM denatured collagen.

27. A method according to claim 24, wherein the effective amount of polar amino acids comprises about 3 to about 150 mM of polar amino acids.

28. A method according to claim 27, wherein the effective amount of polar amino acids comprises about 10 to about 65 mM of polar amino acids.

29. A method according to claim 24, wherein the polar amino acids are selected from the group consisting of arginine, glutamic acid, lysine and mixtures thereof.

30. A method according to claim 29, wherein the matrix comprises:
- about 2 to about 60 mM of L-glutamic acid;
- about 0.5 to about 30 mM of L-lysine; and
- about 1 to about 40 mM of arginine.

31. A method according to claim 24, wherein the matrix further comprises about 5 to about 500 $\mu$M of L-cysteine.

32. A method according to claim 31, wherein the matrix comprises about 15 to about 25 $\mu$M of L-cysteine.

33. A method according to claim 24, wherein the matrix comprises about 5 to about 500 $\mu$M of an L-arginine analogue.

34. A method according to claim 24, wherein the matrix comprises about 15 to about 25 $\mu$M of an L-arginine analogue.

35. A method according to claim 24, wherein the L-arginine analogue comprises aminoguanidine.

36. A method according to claim 24, wherein said introducing step comprises injecting the transplant into a host organism.

* * * * *

UNITED STATES PATENT AND TRADEMARK OFFICE
CERTIFICATE OF CORRECTION

PATENT NO. : 6,315,994 B2
DATED : November 13, 2001
INVENTOR(S) : Usala et al.

It is certified that error appears in the above-identified patent and that said Letters Patent is hereby corrected as shown below:

Column 18,
Line 40, "claim 24" should read -- claim 33 --.

Signed and Sealed this

Twentieth Day of August, 2002

Attest:

JAMES E. ROGAN
Attesting Officer
Director of the United States Patent and Trademark Office